United States Patent [19]

Baasner et al.

[11] Patent Number: 4,533,776

[45] Date of Patent: Aug. 6, 1985

[54] PREPARATION OF FLUORINATED NITROALKANES

[75] Inventors: Bernd Baasner; Hermann Hagemann, both of Leverkusen; Erich Klauke, Odenthal, all of Fed. Rep. of Germany

[73] Assignee: Bayer Aktiengesellschaft, Leverkusen, Fed. Rep. of Germany

[21] Appl. No.: 575,649

[22] Filed: Feb. 1, 1984

[30] Foreign Application Priority Data

Feb. 16, 1983 [DE] Fed. Rep. of Germany ....... 3305201

[51] Int. Cl.$^3$ .............................................. C07C 79/12
[52] U.S. Cl. ..................................... 568/946; 568/945; 568/936
[58] Field of Search ..................... 568/936, 945, 946; 544/204, 197; 71/93

[56] References Cited

U.S. PATENT DOCUMENTS

| | | | |
|---|---|---|---|
| 2,447,504 | 8/1948 | Hass et al. ........................ | 568/945 |
| 2,864,853 | 12/1958 | Bachman et al. . | |
| 3,118,004 | 1/1964 | Hauptschein et al. . | |
| 3,127,736 | 4/1964 | Bost et al. ........................ | 568/945 |
| 3,274,264 | 9/1966 | Graff et al. ...................... | 568/945 |
| 3,441,619 | 4/1969 | Gardner et al. .................. | 568/945 |
| 4,115,459 | 9/1978 | Grant ................................ | 568/945 |
| 4,120,904 | 10/1978 | Pilipovich et al. .............. | 568/945 |
| 4,459,151 | 7/1984 | Kühle et al. ..................... | 71/93 |

FOREIGN PATENT DOCUMENTS

| | | | |
|---|---|---|---|
| 892442 | 6/1944 | France . | |
| 1206389 | 9/1970 | United Kingdom ............. | 568/936 |
| 47908 | 8/1979 | U.S.S.R. .......................... | 568/936 |

OTHER PUBLICATIONS

Chem. Abstracts, CA62:14490b, Columbus, Ohio, USA.
Chem. Abstracts, CA59:12626c, Columbus, Ohio, USA.
A. I. Titov, "Der Ionenmechanismus . . . ", Doklady Akademii Nauk SSSR, Band 149, No. 2, 1983, pp. 330-333.
I. L. Knunyants et al., "Aliphatische . . . ", Izvestiya Akademii Nauk SSSR, Seriya Khimicheskaya, 1963, pp. 1946-1950.
Chemical Abstracts, Bank 62, No. 12, Jun. 7, 1965, Columbus, OH, USA, I. V. Martynov et al., "Halo--nitro carboxylic . . . ", vol. 35, No. 2, (1965), pp. 248-250.
E. R. Bisell et al., "Fluorine-containing Nitrogen Compound . . . ", Tetrahedron, vol. 26, pp. 5737-5743, Pergamon Press, 1970-U.K.

Primary Examiner—Ben R. Padgett
Assistant Examiner—T. J. Wallen
Attorney, Agent, or Firm—Sprung, Horn, Kramer & Woods

[57] ABSTRACT

In the preparation of an α-fluorinated nitroalkane of the formula

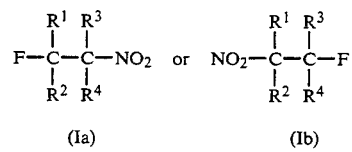

in which
$R^1$, $R^2$, $R^3$ and $R^4$ are identical or different and individually represent hydrogen, fluorine, chlorine, bromine, alkyl, halogenoalkyl or cycloalkyl, or
$R^1$ and $R^3$ have the meaning indicated and
$R^2$ and $R^4$ together represent an alkylene group having 3-6 carbon atoms, by conjugated nitrofluorination of the corresponding olefin of the formula

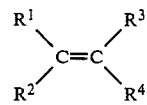

the improvement which comprises employing about 1.1 mols of hydrogen fluoride and 1 to 2 mols of nitric acid per mol of olefin and carrying out the reaction in the presence of an agent which binds water, e.g. chlorosulphonic acid, fluorosulphonic acid, sulphur trioxide, sulphur dioxide, thionyl chloride, thionyl fluoride, sulfuryl chloride or sulfuryl fluoride. The end products, some of which are known, are useful as intermediates in synthesizing herbicides.

19 Claims, No Drawings

PREPARATION OF FLUORINATED NITROALKANES

The invention relates to an improved process for the preparation of α-fluorinated nitroalkanes and -cycloalkanes by conjugated nitrofluorination of the corresponding olefines. Some of the α-fluorinated nitroalkanes which can be prepared according to the invention are already known and can be used as intermediates for the preparation of certain herbicides.

Fluorinated nitroalkanes can be prepared by various processes, for example by reaction of aliphatic carboxylic acids, which contain nitro groups, with SF₄/BF₃ (compare Tetrahedron 26, page 5737 (1970)). The necessary starting materials must first be prepared, and the subsequent fluorination process is extremely elaborate and is completely unsuitable for industrial use.

Moreover, it has been disclosed in reports by Russian authors that aliphatic α-fluorinated nitro compounds can be prepared by the reaction of olefins in anhydrous hydrogen fluoride with concentrated nitric acid in accordance with the general equation below:

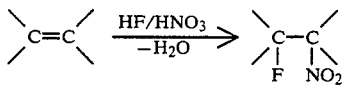

(compare Dokl.Akad.Nauk.SSSR 149, pages 222–5 (1963) (Engl.) and Izvest. Akad.Nauk.SSSR 1963, pages 1794–7 (Engl.)).

This reaction is denoted conjugated nitrofluorination and, in principle, appears attractive for industrial use. However, it emerges that the laboratory procedures known from the Russian publications mentioned are likewise completely unsuitable for direct transfer to large industrial scale.

In the previously known procedure, the hydrogen fluoride acts both as a fluorinating agent and as a solvent and it is employed in very large excess. Since an equimolar amount of water is produced in the reaction, an aqueous mixture of HF and HNO₃ results during the reaction, and this is highly corrosive for the steel stirring vessels which are customarily used. In order to limit this corrosion it is necessary to use a large excess of HF; by this means, the injurious concentration of water can be decreased to such an extent that it is even possible to reach the range of resistance of the materials of the relevant reaction vessels. In the known process, it is necessary to employ 5 to 100 mols of hydrogen fluoride to 1 mol of olefin, in other words at least a 500 mol-% excess. The further processing of the resulting aqueous acid mixture is very cost-intensive and industrially difficult. Recovery of the excess hydrofluoric acid in the anhydrous form, as is necessary for renewed reaction, from the resulting aqueous solution is virtually impossible with reasonable industrial expenditure.

It has now been found, surprisingly, that conjugated nitrofluorination can also be carried out in the presence of agents which bind water, this largely preventing the corrosion, which otherwise occurs, of the steel equipment which is customarily used for reaction vessels.

Thus the invention relates to a process for the preparation of α-fluorinated nitroalkanes of the general formula

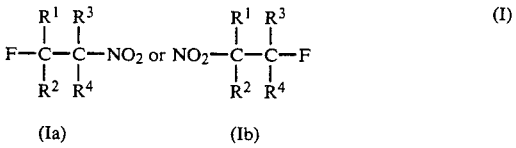

in which,
R¹, R², R³ and R⁴ are identical or different and individually represent hydrogen, fluorine, chlorine, bromine, alkyl, halogenoalkyl or cycloalkyl, or
R¹ and R³ have the meaning indicated and
R² and R⁴ together represent an alkylene group having 3–6 carbon atoms, by conjugated nitrofluorination of the corresponding olefins of the formula

in which,
R¹, R², R³ and R⁴ have the meaning indicated above, characterized in that the reaction is carried out in the presence of an agent which binds water, it being possible to use customary steel equipment.

It is possible to deduce, using the known Markownikoff rule, whether the products formed have the formula (Ia) or (Ib) or, in exceptional cases, are mixtures of (Ia) and (Ib).

In addition, it has been found that the amount of hydrogen fluoride hitherto necessary for dilution can be reduced to a molar excess of about 20%, relative to olefin (II) employed, without losses in yields occurring.

The water which is produced during the reaction is bound, by the addition of a dehydrating agent or an agent which binds water, to such an extent that corrosion, as is highly likely in the presence of water, of the steel equipment, which is customarily used, is considerably diminished or even completely abolished.

Since, in addition, the reaction according to the invention can be carried out with a considerably lower excess of HF (namely 20 ml-% compared with 500–10,000 mol-% in the previously known procedure), the new process is considerably more favorable in respect of costs and can be carried out industrially with fewer problems than the previously described process. Moreover, some considerably improved yields with shorter reaction times are achieved with the anhydrous method. Furthermore, in the case where excesses of HF greater than 20% are used, it is possible to recover the unused hydrogen fluoride in a simple manner. Thus the process according to the invention is also suitable for industrial utilization, it being possible for customary steel stirring equipment to be used, and this signifies a particular advantage.

The olefins to be employed as the starting materials are generally defined by formula (II). In this formula, R¹, R², R³ and R⁴, which can be identical or different, preferably represent hydrogen, fluorine, chlorine, bromine, alkyl having 1–4 carbon atoms, halogenoalkyl having 1–4 carbon atoms (and preferably with fluorine and chlorine as the halogen atom) or cycloalkyl having 3–8 carbon atoms, or R¹ and R³ represent the radicals indicated above, and R² and R⁴ together represent an alkylene group having 3-4 carbon atoms.

The olefins which can be used according to the invention are already known or can be prepared by generally known methods. For example, the olefins, mentioned below can be employed as starting materials: chloroethene, 1,1-dichloroethene, 1,1-difluoroethene, fluoroethene, tetrafluoroethene, trifluoroethene, 1,2-dichloro-1,2-difluoroethene, trifluoroethene, 1-chloro-1,2-difluoroethene, 1,1-dichloro-2-fluoroethene, ethene, 1-chloro-1-fluoroethene, 1,1-dichloro-2,2-difluoroethene, trichloroethene, 1,2-dichloro-1-fluoroethene, propene, 1,1-difluoropropene, 1,1-dichloropropene, 1-chloro-1-fluoropropene, 2-fluoropropene, 2-chloropropene, 1,1-dichloro-3,3-dimethyl-1-propene, hexafluoropropene, 1,1,3,3,3-pentafluoropropene, 1,1-dichloro-2,3,3,3-tetrafluoropropene, 1,1,2-trichloro-3,3,3-trifluoropropene, 1,1,2,3-tetrachloro-3,3-difluoropropene, 3-chloropropene, 2,3-dichloropropene, 3,3,3-trifluoropropene, bromoethene, 1,1-difluorobutene, 1-chloro-1-fluorobutene, 1,1-dichlorobutene, cyclohexene and 2-(fluoromethyl)-3-fluoro-1-propene.

The process according to the invention is carried out in the presence of a dehydrating agent or an agent which binds water. All agents which bind water and which do not undergo or cause side reactions or decomposition reactions are suitable for the reaction. Examples of particularly suitable agents which bind water are the following compounds: chlorosulphonic acid, fluorosulphonic acid, sulphur trioxide, sulphur dioxide, thionyl chloride, thionyl fluoride, sulfuryl chloride and sulfuryl fluoride.

In principle, the sequence in which the components in the reaction are mixed together for carrying out the process is arbitrary. However, it is particularly advantageous first to introduce a mixture of anhydrous hydrogen fluoride, concentrated nitric acid and the relevant dehydrating agent in a steel stirring vessel and then to add the olefin.

It is true that the excess of hydrogen fluoride compared to the olefin employed can be arbitrarily large, but an amount of 1-5 mols suffices, preferably 1-2 mol and, in the sense of the invention, particularly preferably 1-1.2 mols of hydrogen fluoride per mol of olefine (II) to be reacted. In addition, 1 to 2 mols of nitric acid is employed to 1 mol of olefin (II); a molar ratio of 1 to 1.2 mols of nitric acid per mol of olefin is preferred, and 1 mol of nitric acid per mol of olefin is particularly preferred. The amount of agent which binds water can likewise in principle be arbitrarily large, but it is advantageous to employ 1 mol or one equivalent of the agent which binds water per mol of olefin (II) or per mol of nitric acid respectively.

After first introducing the mixture of acids, the olefin to be reacted is introduced into the reaction vessel at temperatures from −80° to +120° C., preferably from −60° to +80° C., by being passed in, condensed in, added dropwise or injected into the closed reaction vessel. The actual reaction temperatures are likewise between −80° and +120° C., preferably between −20° and +80° C. The reaction takes place under normal pressure or the inherent pressure which builds up in the closed reaction vessel during the course of the reaction. However, it is also possible to operate under elevated pressure, for example up to 50 bar, this pressure being reached by injecting an inert gas, such as nitrogen. The reaction time is 0.5 to 48 hours, a reaction time of 2 to 16 hours generally sufficing.

The reaction mixtures are worked up by known procedures. Thus, when the reaction product separates out as a second phase, it can be separated off and purified by distillation. However, it is also possible to dilute the reaction mixture with water and to obtain the product from this crude solution by extraction with inert organic solvents. After neutralization of residues of hydrofluoric acid which are still present, and after drying the extraction solution, the extractant can be removed by distillation and the pure fluoronitroalkane can be obtained by subsequent distillation under normal pressure or under reduced pressure.

The α-fluoronitroalkanes (I) which can be prepared according to the invention can be used, for example, as intermediates for the preparation of fluorine-containing herbicidal active compounds, for example of the class of sym-triazines. It is possible smoothly to reduce the nitro group in the compounds (I) to the amino group by catalytic hydrogenation, the corresponding α-fluorinated alkylamines or cycloalkylamines thus being obtained in high yields. The latter can be reacted in a known manner with cyanuric chloride or cyanuric fluoride to give known sym-triazines which are substituted by the corresponding fluoroalkylamino groups and are known to have potent herbicidal properties (compare, for example, DE-OS (German Published Specification) No. 3,127,861, DE-OS (German Published Specification) No. 3,218,201 and DE-OS (German Published Specification) No. 3,218,966).

Thus, for example, starting from 1-methyl-2,2,2-trifluoronitroethane, the herbicidal active compound 2-chloro-4-ethylamino-6-(1-methyl-2,2,2-trifluoromethylamino)-s-triazine is obtained by the following routes:

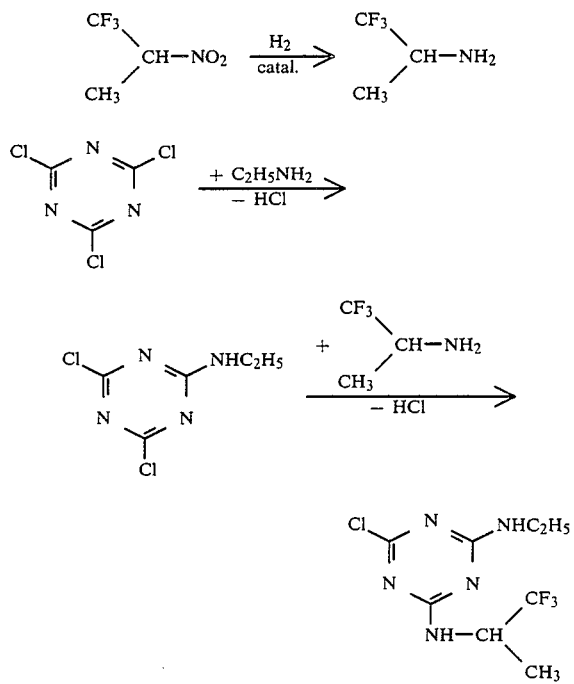

The examples which follow serve to illustrate the invention.

EXAMPLES

Example 1

$CF_3-CH_2-NO_2$ (a) according to the invention:

220 g (11 mols) of hydrogen fluoride, 630 g (10 mols) of nitric acid (d=1.51) and 1,000 g (10 mols) fluorosulphonic acid were introduced first into a V4A stainless steel stirring vessel and, while cooling at $-10°$ to $+10°$ C., 640 g (10 mols) of 1,1-difluoroethene were passed in. The mixture was allowed to reach room temperature and then stirred at this temperature for 4 hours. The reaction mixture was then diluted with 2 liters of water. The organic phase was separated off and the aqueous phase was extracted three times with 200 ml of dichloromethane each time. The combined organic phases were washed with sodium bicarbonate and with water to neutrality, and then dried over magnesium sulphate. After distilling out the solvent, 1,200 g (=93% of theory) of 2,2,2-trifluoronitroethane of boiling point: 91°-92° C.; $n_D^{20}$: 1.3288 were obtained. The figure for corrosion was 2.3 g/m$^2$/day and was thus in the optimum use range for VA stainless steels (compare, for example, the handbook "Böhler-Antinit$^{(R)}$/Chemischbeständige Stähle" (Chemical-resistant steels) Gebr. Böhler & Co. AG Edelstahlwerke, 4000 Düsseldorf-Oberkassel, Hansa-Allee 321; Table G 1).

(b) according to the invention:

A batch with the addition of 1,190 g (10 mols) of thionyl chloride in place of fluorosulphonic acid was carried out in analogy to Example 1(a). 1,120 g (=87% of theory) of 2,2,2-trifluoronitroethane were obtained; boiling point: 91°-93° C.; $n_D^{20}$: 1.3292. The figure for corrosion was 3.9 g/m$^2$/day and was thus also in the most favorable use range for VA stainless steels.

(c) Comparison experiment (according to Izvest-.Akad. Nauk.SSSR 1963, pages 1794-7 (Engl.)):

1,600 g (80 mols) of hydrogen fluoride (anhydrous) and 630 g (10 mols) of nitric acid (d=1.51) were introduced first into a stirring V4A stainless steel autoclave and, while cooling at $-30°$ to $-10°$ C. in ice/salt, 640 g (10 mols) of 1,1-difluoroethene were passed in. The reaction mixture was allowed to come to room temperature in about 4 hours and then poured onto 1.5 kg of ice, and the organic phase was separated off and the aqueous phase was extracted three times with 200 ml of dichloromethane each time. The combined organic phases were washed with sodium bicarbonate solution and with water to neutrality, and then dried over magnesium sulphate. After distilling out the solvent, 790 g (=61% of theory) of 2,2,2-trifluoronitroethane of boiling point 91°-92° C. were obtained; $n_D^{20}$: 1.3285. The figure for corrosion was 16.4 g/m$^2$/day and was thus in the unfavorable use range for VA stainless steels.

The compounds listed in the table below were also prepared in analogy to Example 1(a).

TABLE 1

| Example No. | Olefin (II) | Product (I) | Boiling point [°C.] | $n_D^{20}$ | Yield (%) |
|---|---|---|---|---|---|
| 2 | $CHCl=CH_2$ | $CHClF-CH_2-NO_2$ | 58–60/45 mbar | 1.4290 | 81 |
| 3 | $CCl_2=CH_2$ | $CCl_2F-CH_2-NO_2$ | 56-7/30 mbar | 1.4380 | 92 |
| 4 | $CHF=CH_2$ | $CHF_2-CH_2-NO_2$ | 22/18 mbar | 1.3659 | 82 |
| 5 | $CCl_2=CH-CH_3$ | $CFCl_2-CH(NO_2)-CH_3$ | 54-5/18 mbar | 1.4394 | 76 |
| 6 | $CFCl=CH-CH_3$ | $CF_2Cl-CH(NO_2)-CH_3$ | 34-5/20 mbar | 1.3873 | 88 |
| 7 | $CF_2=CH-CH_3$ | $CF_3-CH(NO_2)-CH_3$ | 99–100 | 1.3380 | 89 |
| 8 | $CHBr=CH_2$ | $CFBrH-CH_2-NO_2$ | 64-5/28 mbar | 1.4642 | 58 |
| 9 | $CH_3-CF=CH_2$ | $CH_3-CF_2-CH_2-NO_2$ | 40-2/25 mbar | 1.3706 | 89 |
| 10 | $CF_2=CFCl$ | $CF_3-CFCl-NO_2$ (64%) + $CF_2Cl-CF_2-NO_2$ (36%) | 36–8 | | 91 |
| 11 | $CH_2=CH_2$ | $CFH_2-CH_2-NO_2$ | 65-6/25 mbar | 1.3018 | 48 |
| 12 | $CF_3-CF=CF_2$ | $CF_3-CF(NO_2)-CF_3$ | 16–18 | | 86 |
| 13 | $CH_3-CH=CH_2$ | $CH_3-CHF-CH_2NO_2$ | 45-6/10 mbar | | 75 |
| 14 | $CFCl=CH_2$ | $CF_2Cl-CH_2-NO_2$ | 55-6/30 mbar | 1.3831 | 86 |
| 15 | $CF_2=CF_2$ | $CF_3-CF_2-NO_2$ | $-2$ to $0$ | | 94 |
| 16 | $CF_2=CFH$ | $CF_3-CFH-NO_2$ | 56 | 1.3010 | 86 |
| 17 | ⌬ (cyclohexene) | cyclohexane with F and NO$_2$ [cis/trans] | 80-3/0.5 mbar | 1.4661 | 51 |
| 18 | $CH_2=C(CH_2F)(CH_2F)$ | $CH_2F-CF(CH_2F)-CH_2NO_2$ | 83-5/20 mbar | 1.3973 | 85 |

TABLE 1-continued

| Example No. | Olefin (II) | Product (I) | Boiling point [°C.] | $n_D^{20}$ | Yield (%) |
|---|---|---|---|---|---|
| 19 | $CF_2=CHCl$ | $CF_3-CHCl-NO_2$ | 79-80 | | 78 |

It is understood that the specification and examples are illustrative but not limitative of the present invention and that other embodiments within the spirit and scope of the invention will suggest themselves to those skilled in the art.

We claim:

1. In the preparation of an α-fluorinated nitroalkane of the formula

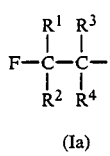    or    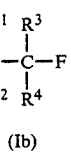

(Ia)                                    (Ib)

in which
R¹, R², R³ and R⁴ are identical or different and individually represent hydrogen, fluorine, chlorine, bromine, alkyl, halogenoalkyl or cycloalkyl, or
R¹ and R³ have the meaning indicated and
R² and R⁴ together represent an alkylene group having 3-6 carbon atoms,
by conjugated nitrofluorination of the corresponding olefin of the formula

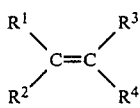

the improvement which comprises carrying out the reaction in the presence of an agent which binds water.

2. A process according to claim 1, wherein the reaction is effected in VA stainless steel.

3. A process according to claim 1, wherein the reaction is carried out at a temperature between about −60° and +120° C.

4. A process according to claim 1, wherein the reaction is carried out at a temperature between about −20° and +80° C.

5. A process according to claim 1, wherein the reaction is carried out at a pressure of about 1 to 50 bar.

6. A process according to claim 1, wherein about 1 to 5 mols of hydrogen fluoride are employed per mol of olefin.

7. A process according to claim 1, wherein about 1 to 1.2 mols of nitric acid are employed per mol of olefin.

8. A process according to claim 1, wherein about 1 mol equivalent of agent which binds water is employed per mol of olefin or per mol of nitric acid.

9. A process according to claim 1, wherein the agent which binds water is chlorosulphonic acid, fluorosulphonic acid, sulphur trioxide, sulphur dioxide, thionyl chloride, thionyl fluoride, sulfuryl chloride or sulfuryl fluoride.

10. A process according to claim 9, wherein the reaction is effected in VA stainless steel at a temperature between about −20° and +80° C. and a pressure of about 1 to 50 bar, employing about equimolar amounts of hydrogen fluoride, nitric acid, olefin and agent which binds water.

11. A process according to claim 1, wherein the olefin is $CF_2=CH_2$ and the α-fluoronitroalkane is $CF_3-CH_2-NO_2$.

12. A process according to claim 1, wherein the olefin is $CHCl=CH_2$ and the α-fluoronitroalkane is $CHClF-CH_2-NO_2$.

13. A process according to claim 1, wherein the olefin is $CCl_2=CH_2$ and the α-fluoronitroalkane is $CCl_2F-CH_2-NO_2$.

14. A process according to claim 1, wherein the olefin is $CHF=CH_2$ and the α-fluoronitroalkane is $CHF_2-CH_2-NO_2$.

15. A process according to claim 1, wherein the olefin is $CF_2=CH-CH_3$ and the α-fluoronitroalkane is $CF_3-CH-CH_3$
         |
         $NO_2$ 16. A process according to claim 1, wherein the olefin is $CHBr=CH_2$ and the α-fluoronitroalkane is $CFBrH-CH_2-NO_2$.

17. A process according to claim 1, wherein the olefin is $CH_3-CF=CH_2$ and the α-fluoronitroalkane is $$CH_3-CF_2-CH_2-NO_2.$$

18. A process according to claim 1, wherein the olefin is $$CH_3-CH=CH_2$$

and the α-fluoronitroalkane is $$CH_3-CHF-CH_2NO_2.$$

19. A process according to claim 1, wherein the olefin is $$CFCl=CH_3$$

and the α-fluoronitroalkane is $$CF_2Cl-CH_2-NO_2.$$

* * * * *